United States Patent
Manevitz et al.

[19]

[11] Patent Number: 5,254,121
[45] Date of Patent: Oct. 19, 1993

[54] METHOD AND DEVICE FOR REMOVING CONCRETIONS WITHIN HUMAN DUCTS

[75] Inventors: Bernard Manevitz, Bronx, N.Y.; George Berci, Los Angeles, Calif.

[73] Assignee: Meditron Devices, Inc., Hackensack, N.J.

[21] Appl. No.: 888,337

[22] Filed: May 22, 1992

[51] Int. Cl.$^5$ .............................. A61B 17/22
[52] U.S. Cl. ..................... 606/128; 606/127; 606/108; 606/29; 606/48; 606/50
[58] Field of Search ............. 128/642; 604/22; 606/1, 606/108, 29, 48, 50, 127, 128

[56] References Cited

U.S. PATENT DOCUMENTS

| | | | |
|---|---|---|---|
| 3,902,499 | 9/1975 | Shene | 606/128 |
| 4,476,862 | 10/1984 | Pao | 606/50 |
| 4,605,003 | 8/1986 | Oinuma et al. | 606/128 |
| 4,785,815 | 11/1988 | Cohen | 128/642 |
| 4,927,275 | 5/1990 | Kriauciunas | 606/128 |
| 5,103,556 | 4/1992 | Filip et al. | 606/128 |
| 5,125,928 | 6/1992 | Parins et al. | 606/48 |

FOREIGN PATENT DOCUMENTS

| | | | |
|---|---|---|---|
| 0866946 | 3/1971 | Canada | 606/128 |
| 2747031 | 5/1979 | Fed. Rep. of Germany | 606/128 |
| 3315303 | 4/1983 | Fed. Rep. of Germany | 606/29 |

OTHER PUBLICATIONS

Krishna Bhatta et al, Effects of Shielded or Unshielded Lasar and Electrohydraulic Lithotripsy on Rabbit Bladder, Apr. 1990, vol. 143 pp. 857-860.

*Primary Examiner*—Stephen C. Pellegrino
*Assistant Examiner*—Glenn K. Dawson
*Attorney, Agent, or Firm*—Malina & Wolson

[57] ABSTRACT

A method and device is described for removing concretions such as calculus stones within human ducts such as the ureter or kidney. The device includes a flexible probe insertable through the human duct so that a tip thereof is juxtaposed against the concretion. The probe includes a positive electrode extending coaxially within the conduit and embedded in a solid electrically insulative material. A negative electrode is coextensive with and outwardly encircles the positive electrode. The solid electrically insulative material stops short by a distance R from the end of the probe, thereby leaving a recess without solid insulation between negative and positive electrodes at the tip end of the probe. The recess achieves a more efficient fragmentation of target calculi at lower energy, with less human tissue damage and increase in useful probe life.

10 Claims, 1 Drawing Sheet

METHOD AND DEVICE FOR REMOVING CONCRETIONS WITHIN HUMAN DUCTS

BACKGROUND OF THE INVENTION

1. Field of the Invention

The present invention relates to a method and device for fragmenting concretions in human ducts.

2. The Related Art

The technique of using high voltage electrical discharge in a fluid medium to create a shockwave capable of fragmenting rocks was developed in the Soviet Union as an industrial technique over 35 years ago. In the early 1960's, the Soviets successfully applied the principles of electrohydraulic lithotripsy (EHL) in the treatment of bladder calculi. As early as 1973, attempts were made to apply this technique to the treatment of ureteral calculi.

U.S. Pat. No. 4,027,674 and U.S. Pat. No. 4,030,505 are typical of the known art. Therein is described a method and device for catheterization within human ducts so as to remove concretions, plaques and sclerotic clots. A series of high voltage pulses of sufficiently low amperage are generated in this method. These pulses are then dispatched through a flexible conduit containing a positive electrode extending coaxially within the conduit embedded in an electrically insulated material and a negative electrode peripherally embedded in the conduit encircling and coextensive with the positive electrode.

Although the use of EHL in treatment of bladder calculi has proved to be a reliable and essentially safe procedure, treatment of ureteral calculi and biliary calculi with this technique is not widely accepted. There are risks associated with the use of existing EHL electrodes in small body lumens such as the ureter and the biliary tree. Moreover, there are difficulties with manipulation and positioning of the probe electrodes in proper proximity to a target calculus. These miniature probes are also of inadequate reliability and have an undesirably short useful life.

Ultra high speed photographic analysis has been used to document the phenomena that actually occurs during the electrohydraulic lithotripsy of a target calculus. When the high voltage discharge occurs across the two electrodes at the tip of the EHL probe within a fluid medium, a small amount of the fluid is vaporized and super heated, turning into a rapidly expanding gas plasma bubble. The rapid expansion of this gas plasma bubble creates a hydraulic shock wave. A portion of the energy in this shock wave can impact a target calculus in close proximity to the tip of the probe, and can cause the calculus to crack into fragments.

Unfortunately, the only portion of the expanding gas bubble that is effective in transferring energy from existing probes to the target calculus is the small percentage travelling along the axis from the surface of these electrode probes to the closest portion of the target calculus. Since existing probes are generally flat across the electrode surface, whether the electrodes are parallel or coaxial, the largest portion of the energy of the expanding gas plasma bubble is dissipated radially away from this axis to the target, and does not contribute to the fragmentation of the calculus.

The inefficiency of existing EHL probes requires that clinical users employ high total energy levels to have adequate energy transfer to the target calculus. If the tips of existing probes are placed too close or in direct contact with the calculus, insufficient fluid medium may be present to allow formation of an effective gas plasma bubble and shock wave. The heat created by high voltage discharge under these circumstances only serves to heat the materials of the probe and surrounding body tissue. Within confined body structures, like the lumen of the ureter or the biliary tree, it has been well documented through clinical experience that the excessive amounts of total energy delivered via existing probes can cause damage to these delicate body tissues. Furthermore, the materials selected for construction of existing probes do not tolerate these high energy discharges creating temperatures in excess of 500° F. without structural damage to these probes.

The insulation materials used to separate the electrodes on existing probes is typically of the thermoplastic type routinely used in the electronics industry as general purpose electrical insulation. These materials tend to melt and shrink due to the instantaneous high temperatures created by high voltage discharge across the probe electrodes. The electrode materials used in existing probes are typically of the types chosen for ease of handling and assembly in the electronics industry, i.e., copper, copper alloys like beryllium copper, and phosphorous bronze. These metals tend to erode easily, and to actually transfer material between electrodes due to the high voltage discharges across the probe electrodes.

These changes to the insulation separating the probe electrodes, and to the electrodes themselves, further decreases the efficiency of the lithotripsy effect obtainable from existing probes. This requires the clinical user to further increase the intensity of the total energy level delivered in an attempt to maintain usable electrohydraulic lithotripsy effect. This, in turn, increases the risk of damage to sensitive surrounding body tissue. The useful life of existing probes is often insufficient to allow completion of the desired lithotripsy treatment. The replacement of damaged electrode probes unnecessarily extends the time required for completion of the clinical procedure.

Accordingly, it is an object of the present invention to provide a device and method for use in electrohydraulic lithotripsy which achieves a more efficient fragmentation of target calculi and requires a lower total energy level.

Another object of the present invention is to provide a device and method for use in electrohydraulic lithotripsy that delivers less energy to surrounding sensitive tissue surfaces and thereby minimizes damage to such surfaces.

A still further object of the present invention is to provide a device and method for use in electrohydraulic lithotripsy that resists the damaging effects of high temperatures created by high voltage discharge across the electrodes and that resists the transfer of materials between electrodes.

A still further object of the present invention is to provide a device and method for use in electrohydraulic lithotripsy that includes a probe having an increased useful life and have a construction of smaller diameter that nevertheless is equivalent in effectiveness to known larger diameter probes.

A still further object of the present invention is to provide a device and method for use in electrohydraulic lithotripsy which does not require positioning of the probe tip in precise distance from a target calculus surface and that achieves effective EHL when in direct contact with the surface of a target calculus.

SUMMARY OF THE INVENTION

A method and device for removing concretions from human ducts is provided. The device includes a flexible probe having first and second ends at opposite termini formed of inert material extendible within the ducts to a situs of the concretions. The probe includes a flexible first and second electrode. The flexible first electrode extends coaxially along a length of the probe and is embedded in a solid electrically insulative material. The flexible second electrode is peripherally arranged radially outward from the first electrode as a continuous electrically conductive surface encircling and coextensive with the first electrode. The first and second electrodes terminate at the first end of the probe while the electrically insulative material terminates short of the first end. Also included within the device is a generator of electrical pulses connected at a second end of the conduit to the positive electrode such that electrical discharges radiate from the first electrode outwardly to the encircling second electrode across a surface of the concretions.

BRIEF DESCRIPTION OF THE DRAWING

The above features, advantages and objectives of this invention will become more readily apparent from the following specific description, reference being made to the accompanying diagrammatic drawing in which.

DETAILED DESCRIPTION

Figure 1:
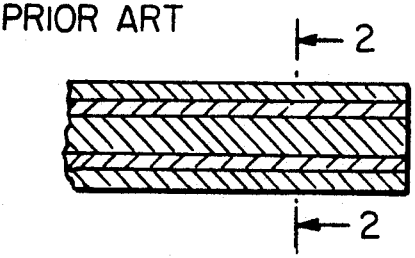
FIG. 1 is a partial cross-sectional view of a prior art probe with parallel electrodes.
Figure 2:
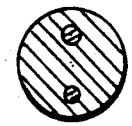
FIG. 2 is a cross-sectional view along lines 2—2 of the probe shown in FIG. 1.
Figure 3:
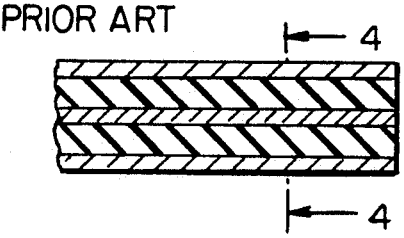
FIG. 3 is a cross-sectional view of a prior art probe with coaxial electrodes.
Figure 4:
FIG. 4 is a cross-sectional view taken along line 4—4 of the probe shown in FIG. 3.

The present invention is best understood when compared to the prior art devices shown in FIGS. 1-4. In one known device illustrated in FIGS. 1-2, the electrodes are a pair of wires oriented parallel to one another. Another known configuration is depicted in FIGS. 3-4 where a central electrode wire is coaxially encircled by a second electrode sheath, each of these electrodes being separated by an electrically insulative material.

Figure 5:
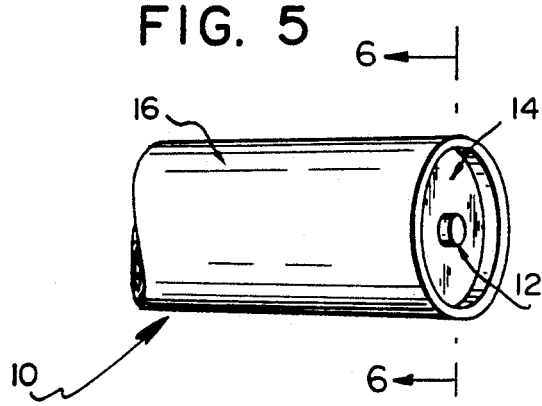
FIG. 5 is a partial elevational view showing a distal portion of a preferred embodiment of the invention.

The present invention improves upon the known art through a probe having a special electrode tip arrangement shown in FIG. 5. The improved EHL coaxial electrode probe is in the form of a flexible conduit 10 as is shown in FIG. 5. Conduit 10 is formed with a flexible first electrode 12 (e.g. positive electrode) extending coaxially within the conduit and being embedded in a solid electrically insulative material 14. Additionally, the conduit includes a flexible second electrode 16 (e.g. negative electrode) peripherally embedded in the conduit radially outward from the first electrode 12 and provides a continuous electrically conductive surface encircling and being coextensive with the first electrode.

The material of the first electrode is chosen for its high temperature melting point and resistance to erosion under high voltage sparking conditions. Tungsten is the preferred material. The electrically insulative material is also chosen for its high temperature melting point, resistance to erosion under high voltage sparking conditions, and further for its ability to maintain the electrical insulating characteristics at high temperatures. Ceramics are the materials of choice for this application. The second or outer electrode is also chosen for its high temperature melting point, high tensile strength, and resistance to erosion under high voltage sparking conditions. Stainless steel is here preferred. These dissimilar conductive substances, e.g. different metals, are chosen for the two electrodes to eliminate any affinity for exchange of material from one electrode to another during high voltage discharge.

Figure 6:
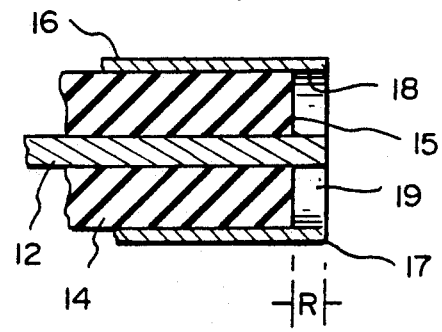
FIG. 6 is a cross-sectional view taken along line 6—6 of the distal portion shown in FIG. 5.
Figure 7:
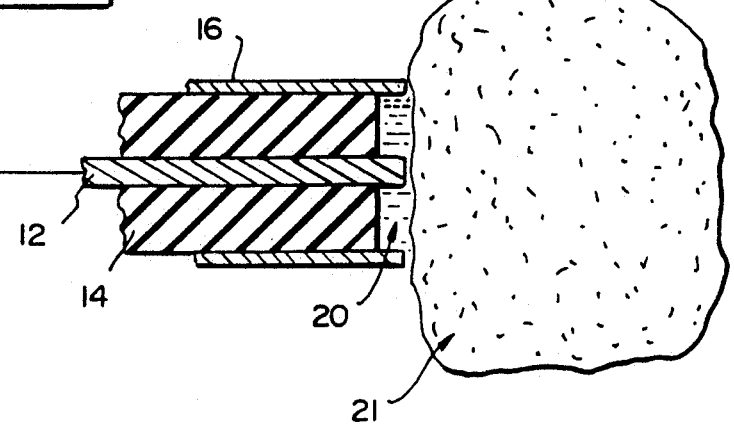
FIG. 7 is a cross-sectional view of the distal portion of the probe shown in FIG. 5 contacting a target calculus.

The key improvement of the present invention lies with the arrangement at the tip end of conduit 10. FIG. 6 shows that the solid electrically insulative material 14 terminates in a surface 15 that is retracted a distance R from the most distal leading edge 17 of the second or outer electrode 16. Retracted surface 15 defines along with an inner surface of the electrode 18 a recess 19 which is devoid of any solid insulative material. Distance R may range anywhere from about 0.0001 to about 10 mm, preferably from about 0.01 to 3 mm. Recess 19 can receive a fluid medium 20 to be captured therewithin when the tip end of the EHL electrode is close to, or in direct contact with, a surface of a target calculi 21 as illustrated in FIG. 7. The fluid medium may either be a bodily fluid within the human duct or a flushing fluid medium delivered exteriorally, such as delivered through an outer annulus of flexible conduit as described in U.S. Pat. No. 4,027,674 herein incorporated by reference.

Besides the probe in the form of a flexible conduit, the device of the present invention will also include a source for generating an electrical pulse to which the conduit is attached. Exemplative of a pulse generator 22 is an apparatus that includes a 3-amp slow-blow dual pole switch, a time delay, a foot switch, a 47 K ¼ W or similar resistor, employed together with a NE 51 H glow lamp, a 120 volt 2.25 amps variable transformer, meter rectifier assembly, and high voltage assembly.

The method for removing concretions within human ducts according to the present invention involves the following steps. Conduit 10 is inserted through a duct such as the ureter so that a tip thereof can be juxtaposed against a concretion in the area with the kidney or bladder. A series of high voltage pulses of amperage of sufficiently short duration, i.e. pulse width to avoid harm to human tissues is generated in the electrical pulse generator 22. Pulses therefrom are directed from one end to another of flexible conduit 10 along a first or inner positive electrode 12 to the situs of the concretion at the tip end of the conduit. Pulses are then selectively discharged radially outwardly across recess 19 between positive and negative electrodes. A liquid within or adjacent recess 19 receives the discharging pulses which cause the fluid to vaporize and have a hydroelectric impact against the concretions.

While the invention has been described in combination with the embodiments thereof, it is evident that many alternative modifications and variations will be apparent to those skilled in the art in light of the foregoing description. Accordingly, it is intended to embrace all such alternatives, modifications, and variations as fall within the spirit and broad scope of the appended claims.

What is claimed is:

1. A device for removing concretions within human ducts comprising:
    a flexible probe having first and second ends at opposite termini thereof and being of inert material and of sufficiently small diameter to be deployable within said ducts including a ureter to a situs of said concretions, said probe comprising:
        a flexible first electrode extending axially along a length of said probe and being embedded in a solid electrically insulative material; and
        a flexible second electrode arranged radially outward from said first electrode as a continuous electrically conductive surface encircling and coextensive with said first electrode, said first and second electrodes terminating at said first end of said probe while said electrically insulative material terminates short of said first end by a length of from 0.01 to 10 mm; and
    a means for generating an electrical pulse connected at said second end of said probe to one of said electrodes such that electrical discharges radiate from one of said electrodes to said other electrode across a surface of said concretions.

2. A device according to claim 1 wherein said first and second electrodes are positive and negative electrodes, respectively.

3. A device according to claim 1 wherein said first electrode is formed of Tungsten.

4. A device according to claim 1 wherein said second electrode is formed of stainless steel.

5. A device according to claim 4 wherein said solid electronically insulative material is a ceramic.

6. A device according to claim 1 wherein said first and second electrodes are formed of different electrically conductive substances.

7. An electrohydraulic lithotripsy probe for use with a device to remove concretions within human ducts, said probe having first and second ends at opposite termini thereof and being of inert material and of sufficiently small diameter to be deployable within such ducts to a situs of said concretions comprising:
    a flexible first electrode extending coaxially along a length of said probe and being embedded in a solid electrically insulative material; and
    a flexible second electrode arranged radially outward from said first electrode as a continuous electrically conductive surface encircling and coextensive with said first electrode, said fist and second electrodes terminating at said first end of said probe while said electrically insulative material terminates short of said first end by a length of from 0.01 to 10 mm.

8. A method for removing concretions within human ducts comprising:
    (i) inserting a flexible probe through said ducts to a situs of said concretions, said probe having first and second ends at opposite termini thereof, being of inert material and comprising:
        a flexible first electrode extending coaxially within said probe and being embedded in a solid electrically insulative material; and
        a flexible second electrode arranged radially outward from said first electrode as a continuous electrically conductive surface encircling and coextensive with said first electrode, said first and second electrodes terminating at said first end of said conduit while said electrically insulative material terminates short of said first end to thereby form a recess between an inner wall of said encircling second electrode, a terminating wall of said insulative material and an outer edge of said first electrode;
    (ii) generating in a pulse generator a series of high voltage pulses providing amperage pulses of sufficiently short duration to avoid harm to human tissues;
    (iii) directing said pulses from said pulse generator into said flexible probe at said second end along one of said electrodes down to said first end placed adjacent to said situs of said concretions, a fluid being collected at said recess; and
    (iii) discharging said pulses between said first and second electrodes within said recess so as to energize said fluid thereby causing said fluid to direct a hydroelectric impact against said concretions to achieve a efficient fragmentation of said concretions.

9. A method according to claim 8 wherein said electrically insulated material terminates short of said first and second electrodes by a length of 0.01 to 10 mm.

10. A method according to claim 8 wherein said first and second electrodes are formed of different electrically conductive substances.

* * * * *